US012286391B2

(12) United States Patent
Hausmann et al.

(10) Patent No.: US 12,286,391 B2
(45) Date of Patent: Apr. 29, 2025

(54) DIESEL EXHAUST FLUID ON DEMAND SYSTEM, APPARATUS, AND METHOD

(71) Applicant: AWA Technology LLC, Kansas City, MO (US)

(72) Inventors: Austin J. Hausmann, Kansas City, MO (US); William L. Walls, III, Overland Park, KS (US); Adam M. Bronge, Ballwin, MO (US)

(73) Assignee: AWA TECHNOLOGY LLC, Kansas City, MO (US)

( * ) Notice: Subject to any disclaimer, the term of this patent is extended or adjusted under 35 U.S.C. 154(b) by 677 days.

(21) Appl. No.: 17/497,670

(22) Filed: Oct. 8, 2021

(65) Prior Publication Data

US 2022/0112828 A1 Apr. 14, 2022

Related U.S. Application Data

(60) Provisional application No. 63/089,873, filed on Oct. 9, 2020.

(51) Int. Cl.
*C07C 273/00* (2006.01)
*B01D 53/92* (2006.01)
(Continued)

(52) U.S. Cl.
CPC ............ *C07C 273/00* (2013.01); *B01D 53/92* (2013.01); *B01F 23/51* (2022.01);
(Continued)

(58) Field of Classification Search
CPC ...... C07C 273/00; B01D 53/92; B01D 61/02; B01F 23/51; B01F 35/7131;
(Continued)

(56) References Cited

U.S. PATENT DOCUMENTS

| 5,971,207 A | * | 10/1999 | McDonough | ......... | B05B 7/1445 |
| | | | | | 222/105 |
| 2005/0284135 A1 | * | 12/2005 | Bertiller | ................ | B01D 53/90 |
| | | | | | 60/286 |

(Continued)

OTHER PUBLICATIONS

International Search Report and Written Opinion in corresponding PCT/US2021/054243, dated Mar. 1, 2022.

*Primary Examiner* — Brandon D Lee
(74) *Attorney, Agent, or Firm* — Hovey Williams LLP; Crissa A. Cook

(57) ABSTRACT

Provided herein are systems, apparatuses, and methods for localized, on-demand diesel exhaust fluid ("DEF") production. The systems can comprise a loading station for securing a container comprising a pre-measured quantity of urea and releasing the urea from the container. The released urea and water can then be fed into a mixing tank to produce the DEF product. The water can be pre-treated, for example, in a reverse osmosis and/or deionization process before being fed to the mixing tank. The DEF product can be immediately dispensed into a diesel vehicle or stored in a nearby intermediate storage tank. The systems and processes advantageously reduce or eliminate the need for over-the-road shipments and retail packaging of DEF.

12 Claims, 16 Drawing Sheets

(51) Int. Cl.
*B01D 61/02* (2006.01)
*B01F 23/50* (2022.01)
*B01F 35/71* (2022.01)
*B01F 35/80* (2022.01)
*B01F 35/88* (2022.01)

(52) U.S. Cl.
CPC .... *B01F 35/7131* (2022.01); *B01F 35/71731* (2022.01); *B01F 35/88* (2022.01); *B01D 61/02* (2013.01); *B01F 35/80* (2022.01); *F01N 2610/02* (2013.01); *F01N 2610/1433* (2013.01)

(58) Field of Classification Search
CPC .... B01F 35/71731; B01F 35/88; B01F 35/80; B01F 35/882; B01F 21/30; F01N 2610/02; F01N 2610/1433; F01N 2610/1406; F01N 2610/1413; F01N 3/2066; Y02A 50/20; Y02T 10/12
See application file for complete search history.

(56) References Cited

U.S. PATENT DOCUMENTS

| | | | |
|---|---|---|---|
| 2010/0084606 A1* | 4/2010 | Arvola | B01D 53/90 252/188.1 |
| 2011/0126514 A1* | 6/2011 | Brammell | G05D 11/132 60/303 |
| 2013/0025265 A1 | 1/2013 | Gundrum | |
| 2016/0368758 A1* | 12/2016 | Brammell | B67D 7/744 |
| 2018/0058984 A1 | 3/2018 | Szymusiak et al. | |
| 2019/0185422 A1 | 6/2019 | Pustjens et al. | |
| 2019/0240627 A1* | 8/2019 | Gautier | B01F 21/30 |
| 2019/0292064 A1 | 9/2019 | Krawczyk et al. | |

* cited by examiner

DIESEL EXHAUST FLUID ON DEMAND SYSTEM, APPARATUS, AND METHOD

CROSS-REFERENCE TO RELATED APPLICATIONS

The present application claims the priority benefit of U.S. Provisional Patent Application Ser. No. 63/089,873, filed Oct. 9, 2020, entitled DIESEL EXHAUST FLUID ON DEMAND SYSTEM, APPARATUS, AND METHOD, incorporated by reference in its entirety herein.

BACKGROUND OF THE INVENTION

Field of the Invention

The present disclosure is generally directed to automotive fluids, and particularly diesel exhaust fluids, and systems, apparatuses, and methods for producing the same.

Description of Related Art

Diesel exhaust fluid ("DEF") is an integral part of the after-treatment system on diesel engines. Beginning in 2010 (following a U.S. Environmental Protection Agency rule making, on-road heavy-duty diesel engines are required to utilize NOx exhaust control technology. A significant majority of diesel engines utilize DEF to meet increasing emissions controls standards. DEF is injected directly into the exhaust stream of vehicles, trains, ships, and equipment to breakdown harmful NOx into less harmful constituents, with the overall goal of improving air quality.

Today DEF is mass produced in a centralized production model and then distributed to end user customers and retail outlets. This route to market is inefficient. By weight, DEF consists of approximately ⅔ deionized water and ⅓ urea. Water is ubiquitous and inexpensive in the developed world, yet the current DEF production model involves shipping it long distances, in mass quantities. Additionally, DEF is primarily shipped in wasteful single use plastics. The most common medium is a 2.5-gallon container with a high packing-to-content ratio. Furthermore, DEF is particularly susceptible to its surroundings. Sunlight, temperature, and humidity all drastically degrade the shelf life which is often undetectable until it is in the vehicle. This can lead to costly repairs, downtime, and wasted product.

SUMMARY OF THE INVENTION

Embodiments of the present disclosure enable a DEF production process in which over-the-road shipments of water can be completely eliminated and overall retail packaging significantly reduced. By utilizing on-site feed water in a hyper local production model, processes and systems in accordance with embodiments described herein can be deployed at point-of-use.

In one or more embodiments, there is provided a process for producing diesel exhaust fluid. The process comprises securing a container comprising a pre-measured quantity of urea into a loading station, forming an opening in the container, thereby releasing the urea from the container through the opening, feeding the urea and water into a mixing tank, and mixing the urea and the water in the mixing tank to produce the diesel exhaust fluid.

In one or more embodiments, there is provided a process for producing and distributing diesel exhaust fluid. The process comprises feeding urea and water into a mixing tank, mixing the urea and the water in the mixing tank to produce the diesel exhaust fluid, and dispensing the diesel exhaust fluid directly into a diesel vehicle without introducing the diesel exhaust fluid into a storage vessel.

In one or more embodiments, there is provided a diesel exhaust fluid production system. The system comprises a loading station configured to receive and secure a container comprising a pre-measured quantity of urea, an opening device configured to form an opening in the container, thereby releasing the pre-measured quantity of urea, and a mixing tank configured to receive and mix the urea and water to produce a diesel exhaust fluid product.

DETAILED DESCRIPTION OF THE PREFERRED EMBODIMENTS

The systems, apparatuses, and processes according to preferred embodiments are described in greater detail below.

It is to be understood, however, that these features do not necessarily limit the overall scope of the invention. Additionally, it should be understood that these features may be included individually or in combination with one or more other features described herein in relation to one or more embodiments within the scope of the invention.

Figure 1:
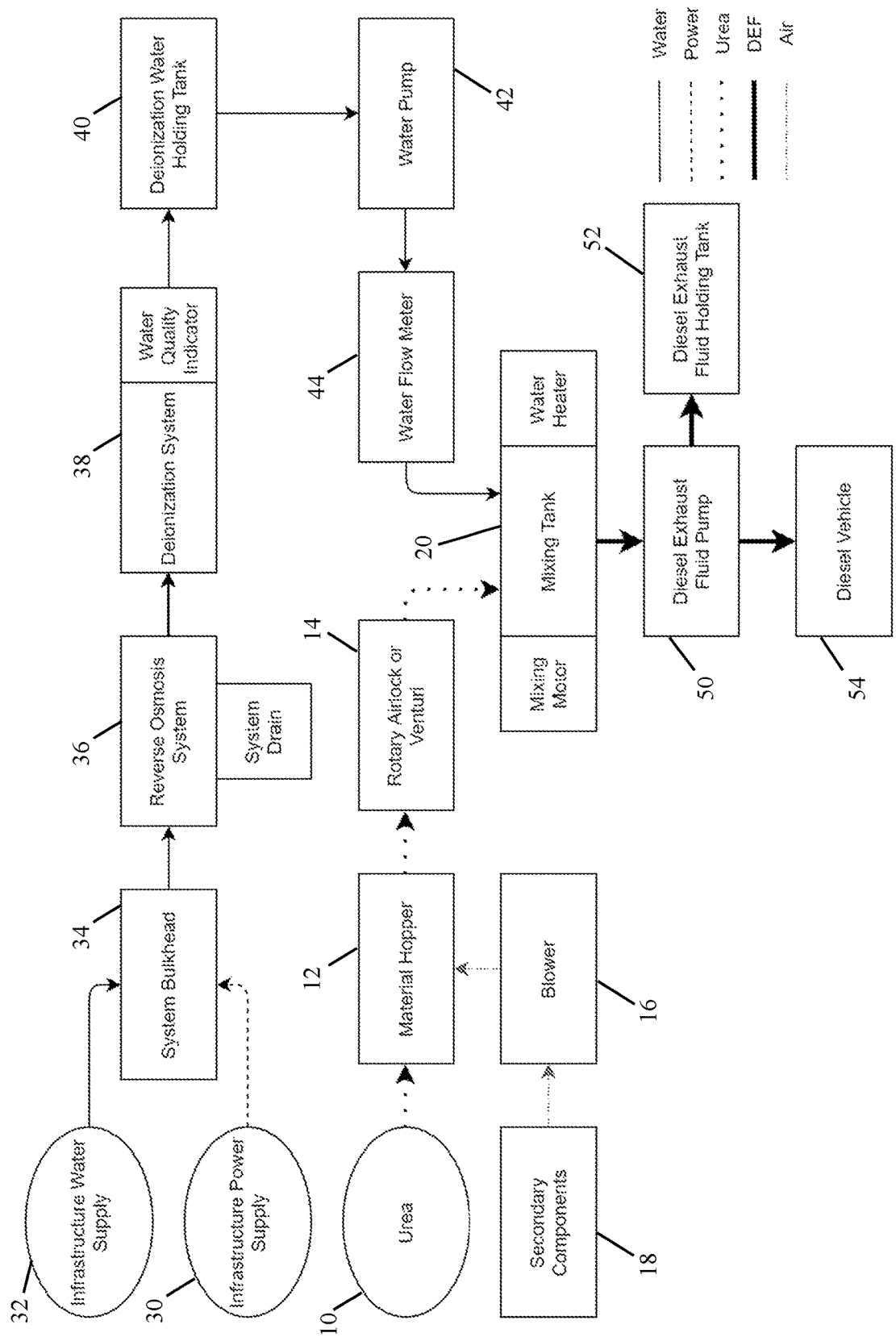
FIG. 1 is a block flow diagram illustrating the main steps of a process and system for producing diesel exhaust fluid according to one or more embodiments of the present invention.

FIG. 1 illustrates an overview of an exemplary process for producing diesel exhaust fluid (DEF) according to certain embodiments of the present invention. As shown in FIG. 1, urea is provided 10 and released into a material hopper 12. The urea is then fed from the hopper 12 to a mixing tank 20, which may be facilitated by a rotary airlock, a venturi, an auger, or other dispensing mechanism 14. In certain embodiments, the hopper 12 comprises an air blower 16, which may be equipped with secondary support components 18, such as an air filtration system and/or silencer. Concurrently, water 30 and power 32 may be supplied to the system bulkhead 34 from existing infrastructure. In certain embodiments, the water may then be treated in a reverse osmosis process 36 and/or deionization process 38 to provide sufficiently pure water that can be used in DEF production. The purified water can be held in a holding tank 40 and distributed as needed. For example, a water pump 42 and flow meter 44 may be used to feed an appropriate amount of water from the holding tank 40 to the mixing tank 20. The urea and water are then mixed in the mixing tank 20 to produce a DEF product. The DEF product is then pumped 50 from the mixing tank to a holding tank 52 and/or directly into a diesel vehicle 54 for use.

Urea Processing

Figure 2:
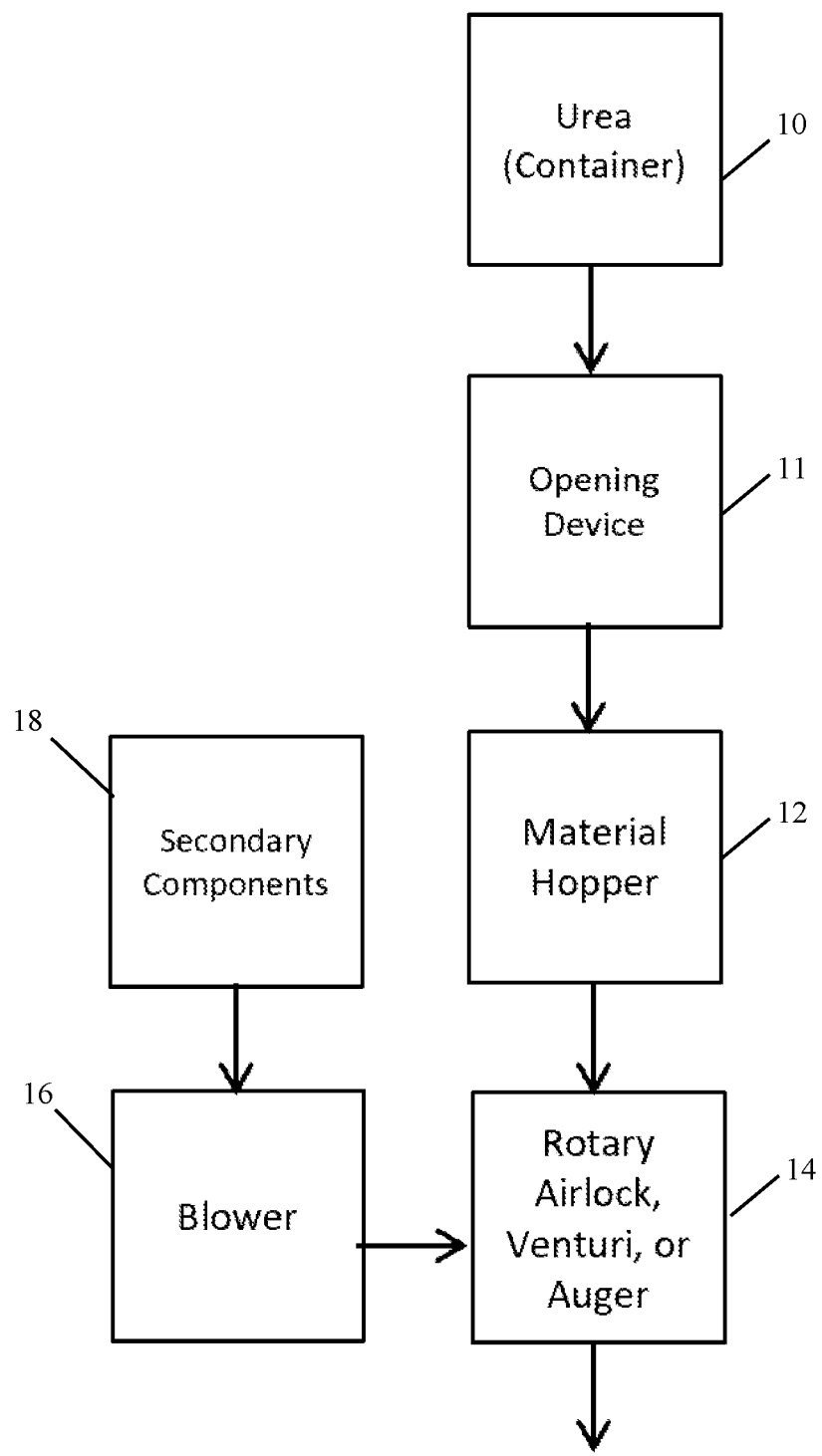
FIG. 2 is a block flow diagram illustrating the main steps of urea processing according to one or more embodiments of the present invention.

As shown in FIG. 2, in certain embodiments, urea processing begins with providing a pre-measured quantity of urea 10. In certain embodiments, the urea is provided as substantially pure urea. For example, in certain embodiments, the urea has a purity of at least 99%, or preferably at least 99.9% by weight. In certain preferred embodiments, the urea is automotive grade equivalent or higher, as specified by ISO 22241. In particular, the urea is preferably an industrially produced grade of urea (CAS Number 57-13-6) which may comprise traces of biuret, ammonia and water, and is free of aldehydes or other substances such as anti-caking agent, and free of contaminants such as sulfur and its compounds, chloride, nitrate or other compounds. In certain other embodiments, the pre-measured quantity of urea is provided as a mixture comprising urea and one or more additives. In certain such embodiments, the mixture comprises at least 25%, at least 50%, at least 75%, at least 80%, at least 85%, at least 90%, at least 95%, or at least 98% by weight urea. In certain embodiments, the urea is provided in the form of powder, prills, pellets, and/or granules. The amount of urea in the pre-measured quantity may be selected depending on the amount and specifications of DEF product being produced. In particular, the amount of urea in the pre-measured quantity may be selected so as to provide a weight ratio with water in the mixing tank of about 1:2 urea-to-water, as described in greater detail below. However, in certain embodiments, the amount of urea in the pre-measured quantity may be selected so as to provide other ratios of urea-to-water, which may be selected depending on the particular application and/or regulations.

In certain embodiments, the pre-measured quantity of urea is provided in a container. In certain embodiments, the contents of the container consist of, or consist essentially of, the pre-measured quantity of urea. The container may be in the form of a pod, box, package, or other carrier capable of holding the solid urea. The container may be secured into a loading station 11, where an opening is formed in the container, thereby releasing the urea from the container through the opening. In certain embodiments, the opening may be formed by piercing, ripping, cutting, and/or tearing the container, which may be facilitated by a manual or automated opening device within the loading station 11. In certain embodiments, the urea may be passively released into the hopper 12, for example by gravity. In certain such embodiments, the container may have a sloped or cone-shaped bottom, so as to allow the urea to passively flow out through the opening. In certain same or other embodiments, a fluid (e.g., air, water) may be passed through the container to facilitate transfer of the urea to the hopper 12 or other downstream processes.

Figure 3A:
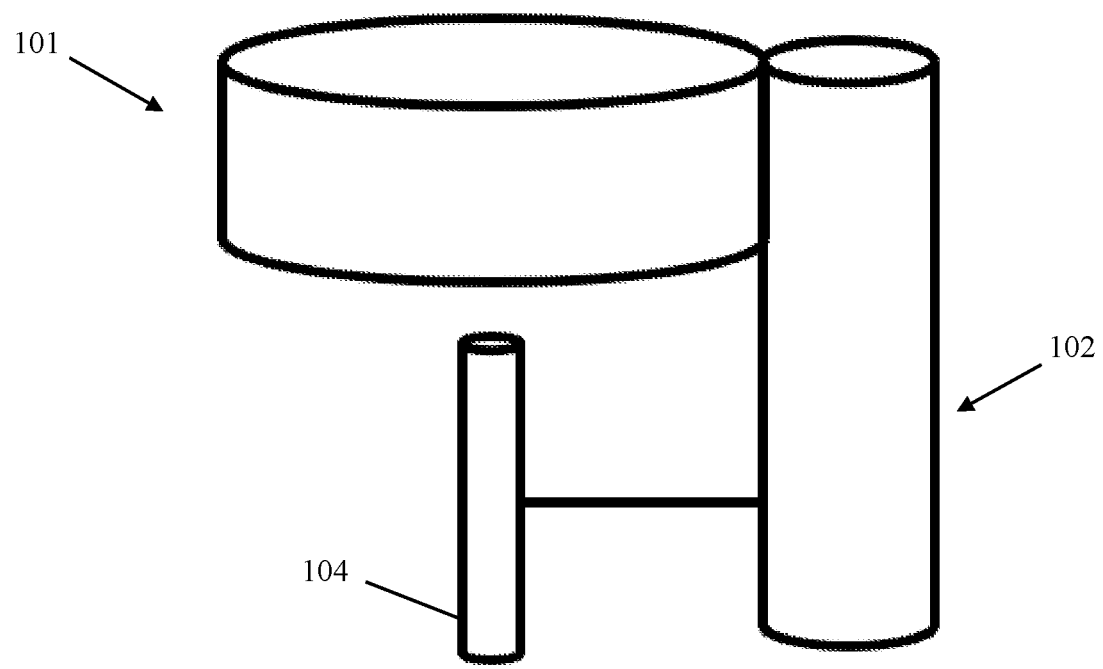
FIGS. 3A-3B show perspective views of an exemplary loading station and opening device according to one or more embodiments of the present invention, with a retracted piercing rod (FIG. 3A) and an inserted piercing rod (FIG. 3B)
Figure 3A:
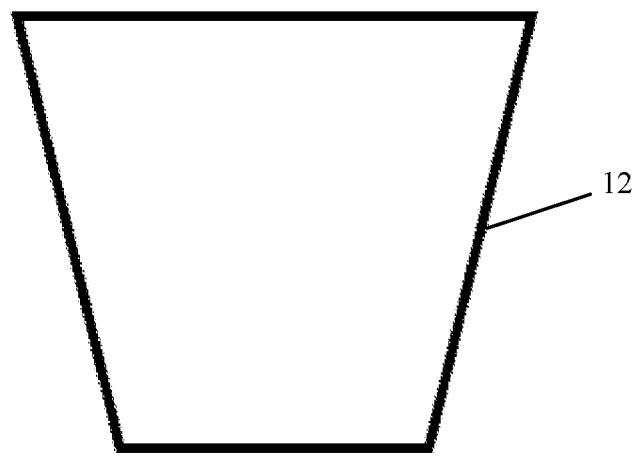
Figure 3B:
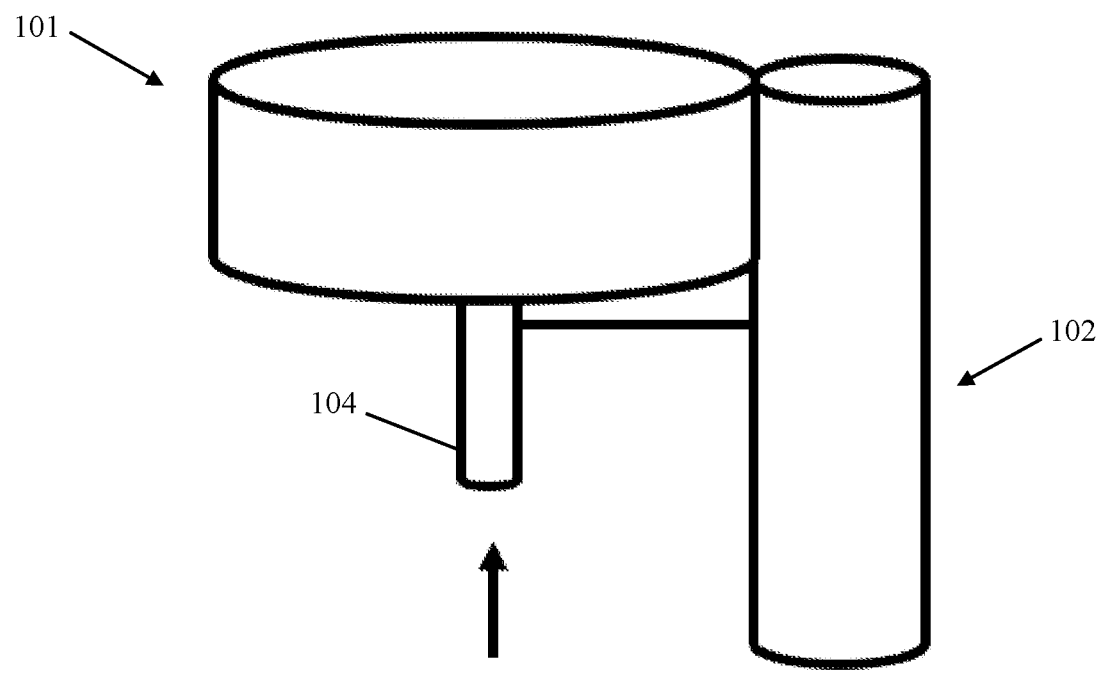
Figure 3B:
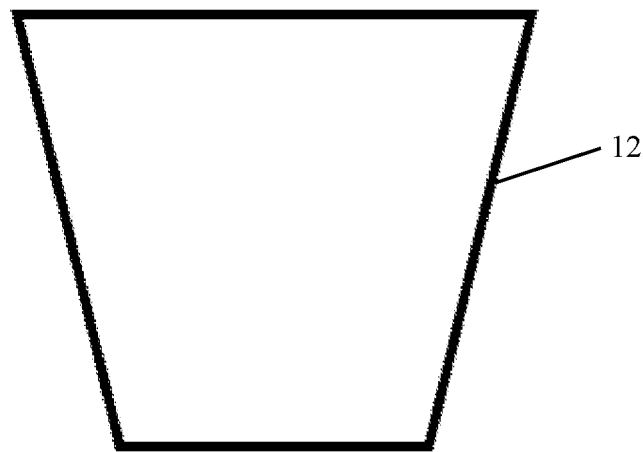
Figure 4A:
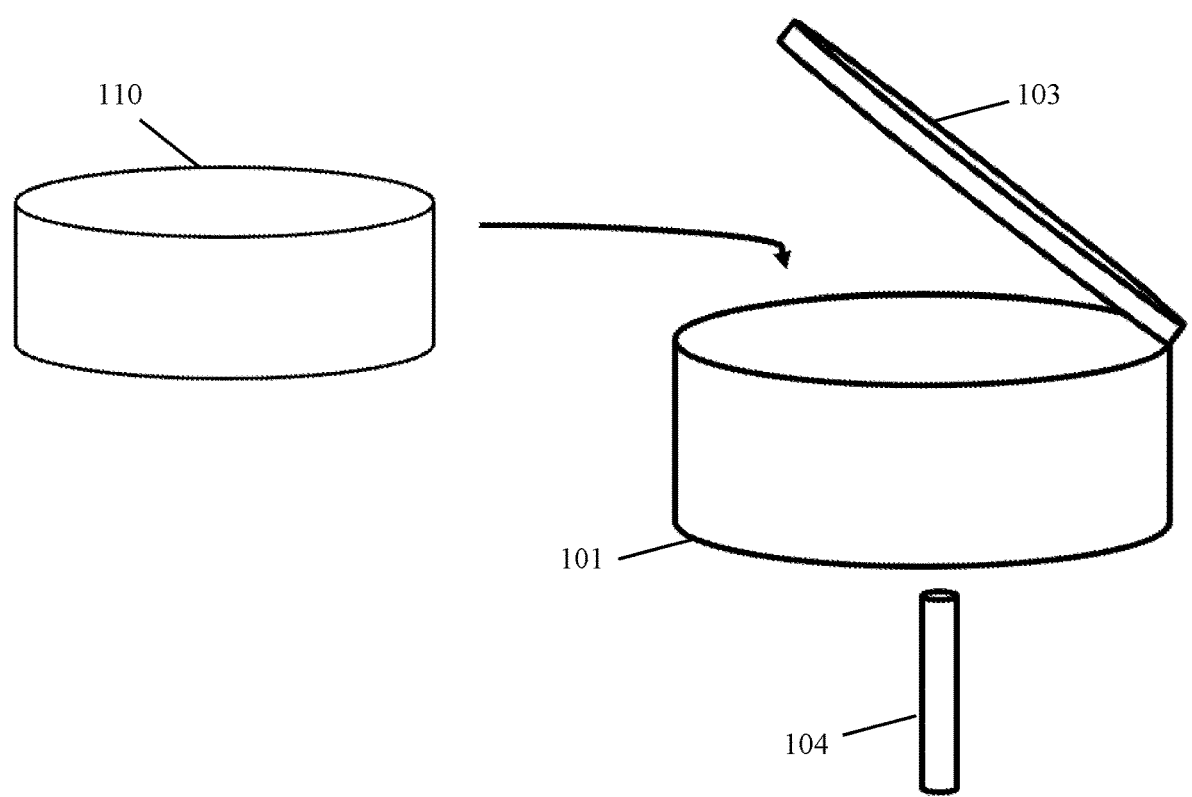
FIGS. 4A-4D show perspective views illustrating the operation of an exemplary loading station and opening mechanism according to one or more embodiments of the present invention, including loading the container into the loading station (FIG. 4A), securing the container within the loading station with a lid (FIG. 4B), forming an opening in the container using a piercing rod (FIG. 4C), and retracting the piercing rod to allow urea to release from the container through the opening (FIG. 4D)
Figure 4B:
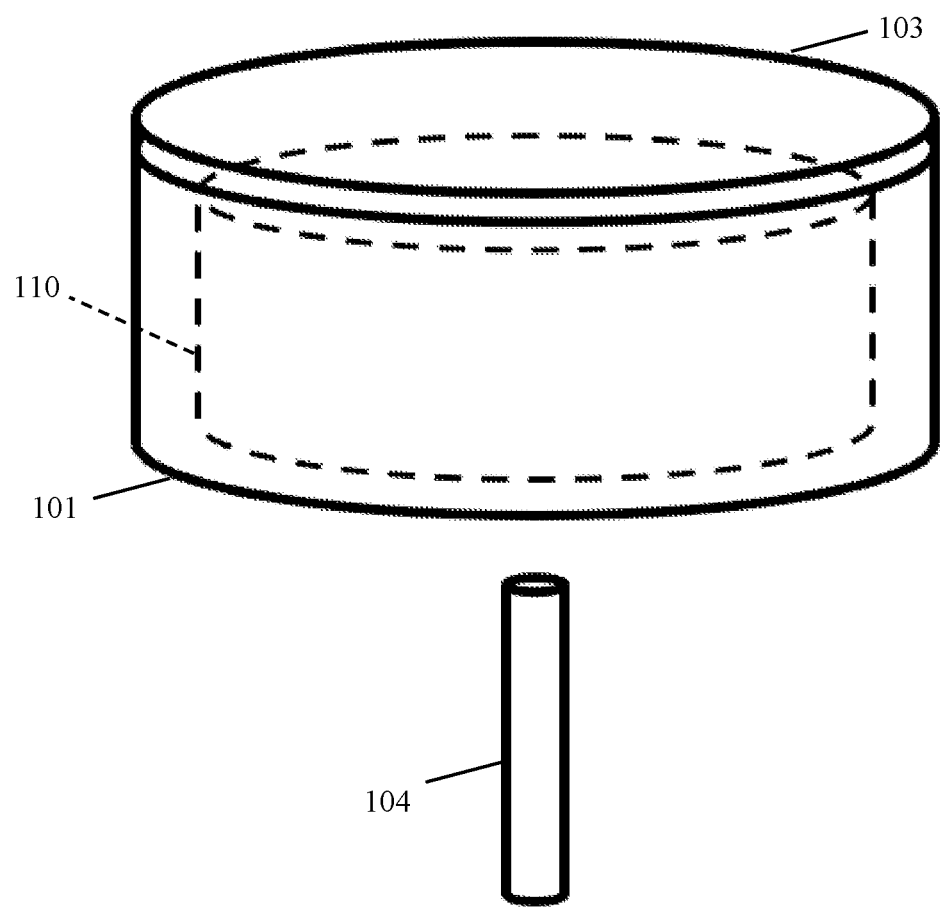
Figure 4C:
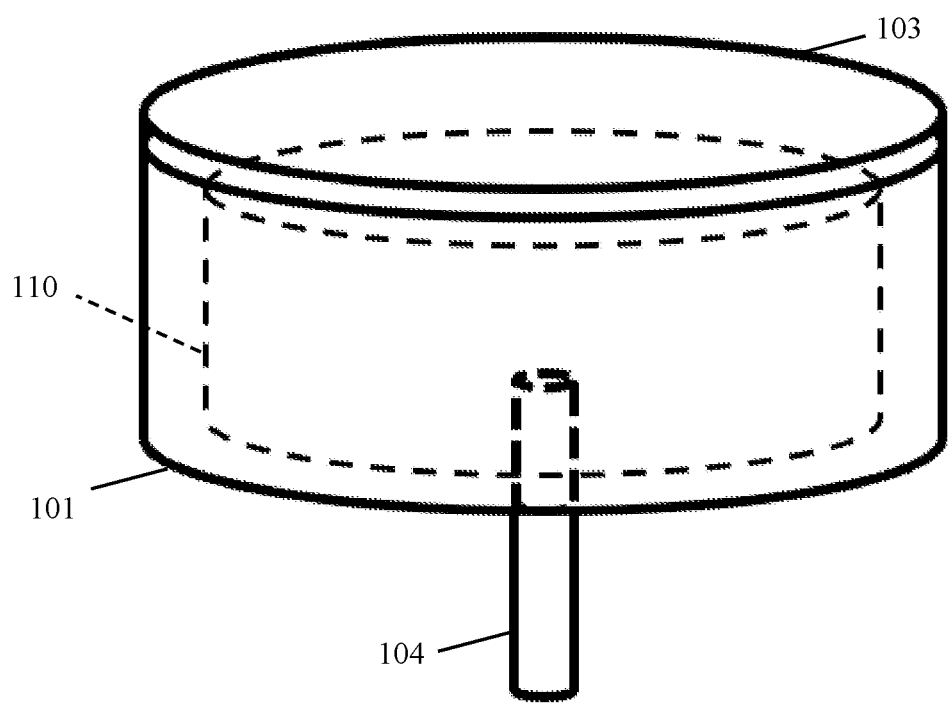
Figure 4D:
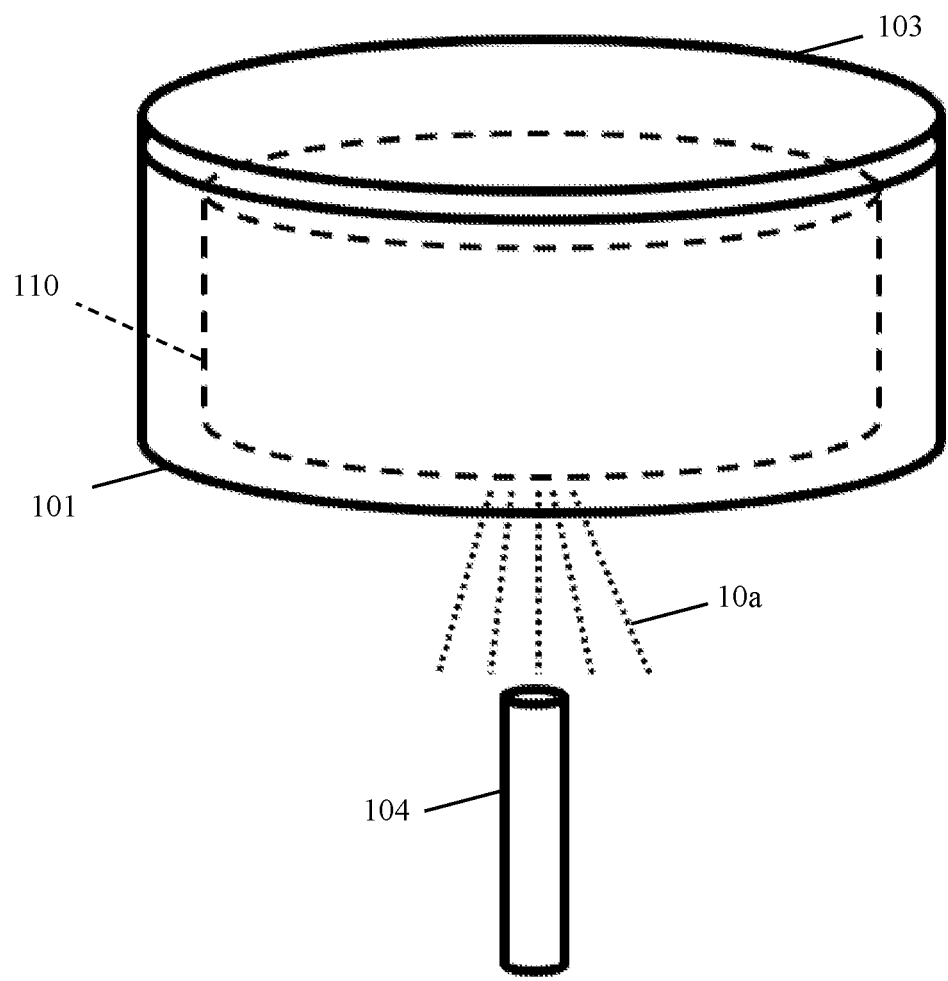

An exemplary loading station 101 and opening device 102 are shown in FIGS. 3A-3B. In the embodiment shown, the opening device comprises a rod 104, which may comprise a sharp point (not shown) on one end, that may be inserted into (FIG. 3B), and retracted from, the loading station 101 to pierce the container. The operation of the opening device 102 is shown in FIGS. 4A-4D. In particular, the container 110 may be manually loaded into the loading station 101 (FIG. 4A) and secured by a lid 103 (FIG. 4B). The rod 104 may be inserted through the bottom of the loading station 101 and into the container 110, thereby piercing the bottom surface of the container 110 and forming an opening therein (FIG. 4C). The rod 104 may then be retracted, thereby releasing the urea 10a from the container 110 and loading station 101 (FIG. 4D).

Figure 5A:
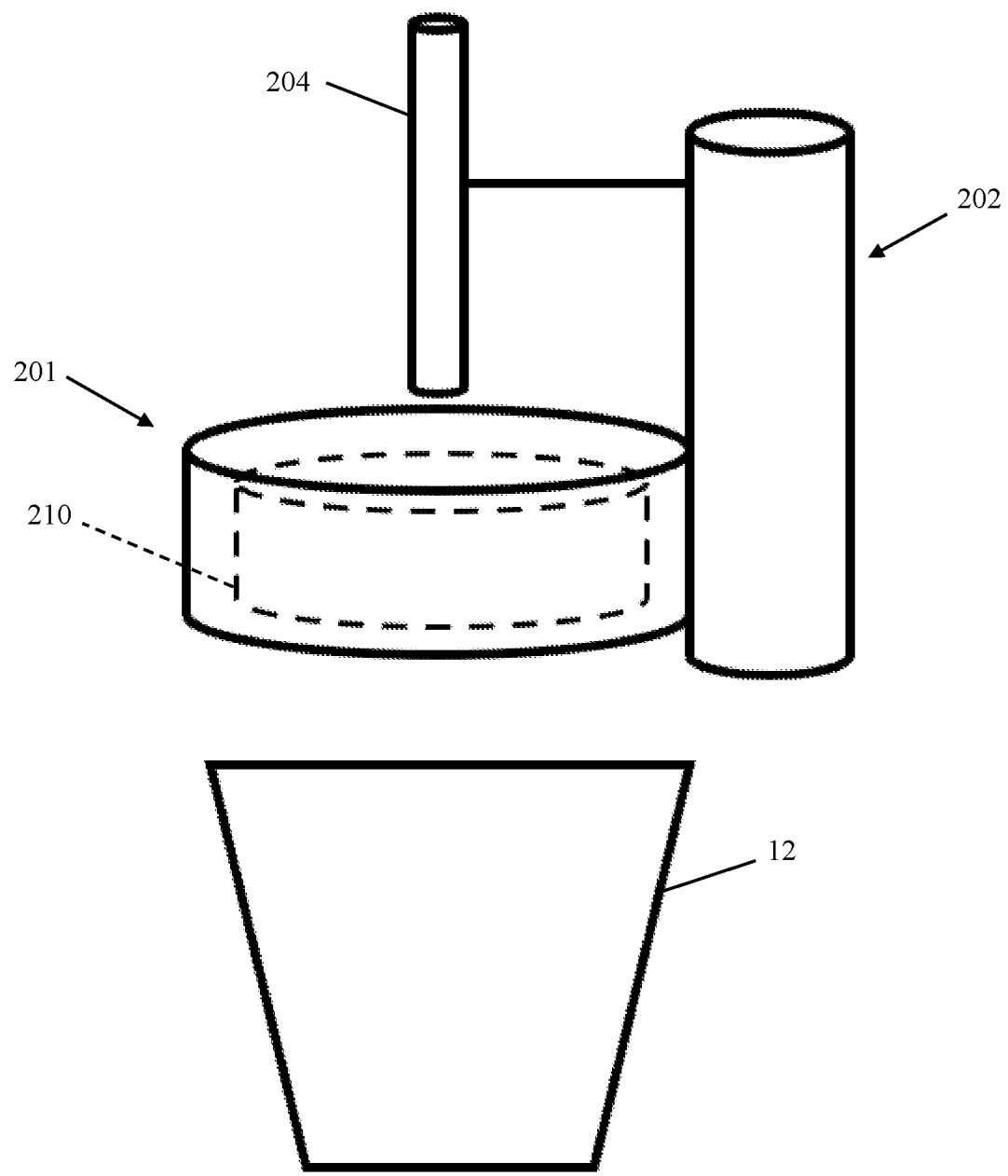
FIGS. 5A-5B show perspective views of an exemplary loading station and container opening device according to one or more embodiments of the present invention, with a retracted piercing rod (FIG. 5A) and a piercing rod inserted from the top through both a top surface and a bottom surface of a container (FIG. 5B)
Figure 5B:
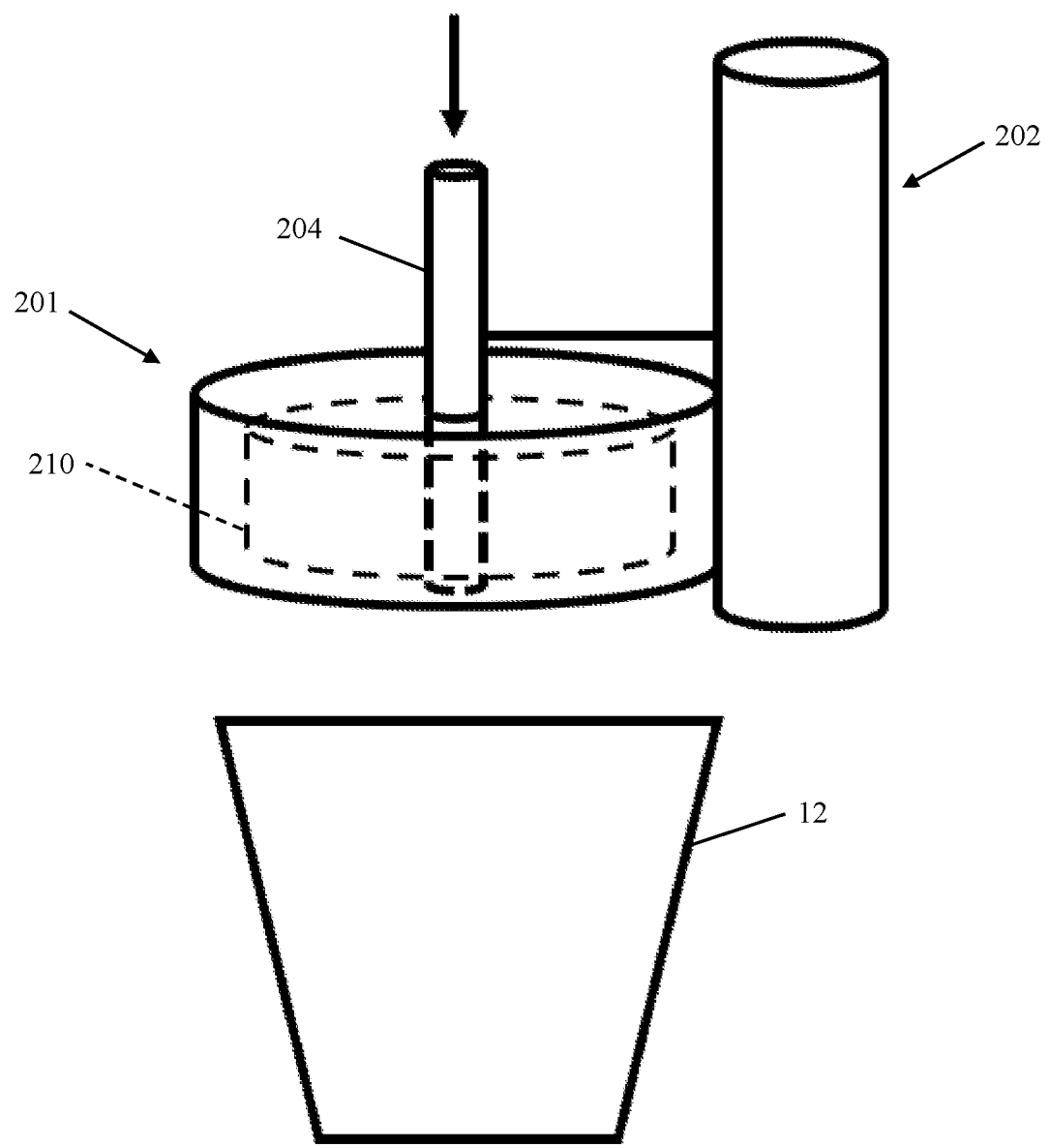

Another exemplary loading station 201 and opening device 202 are shown in FIGS. 5A-5B. In the embodiment shown, the rod 204 may be inserted through the top of the container 210 (FIG. 5B), piercing both the top surface and the bottom surface of the container 210, and retracted from the loading station 201. Such embodiments may allow water or other fluid to be fed through the container to facilitate release of the urea, which may allow for direct transfer of the urea into the mixing tank without including a hopper or other separate feeding mechanism.

Although the embodiments shown in the figures illustrate a rod inserted into the bottom or top of the loading station and piercing the bottom surface of the container, or top and bottom surfaces of the container, it should be understood that in certain embodiments other devices may be used so long as an opening is formed in the container configured to release the urea. For example, in certain embodiments, one or more rods and/or other opening device may be inserted from the top, side, and/or bottom of the loading station to form an opening through the top, side, and/or bottom of the container. Additionally, or alternatively, the opening device may reside partially or entirely within the loading station, which can eliminate or reduce external moving parts. It should also be understood that the container may be loaded into the loading station from the top, side, or bottom.

The urea may be released into the hopper 12, which collects and dispenses the urea into the mixing tank 20. Referring again to FIG. 2, the hopper 12 may comprise a rotary airlock, a venturi, an auger, or other feeder mechanism 14 to dispense the urea from the hopper 12 to the mixing tank 20. In certain embodiments, and particularly when a rotary airlock or venturi distribution mechanism 14 is used, the hopper 12 may comprise a blower 16, which may be equipped with secondary support components 18, such as an air filtration system and/or silencer. The blower 16 may be included, for example, to dry the urea and/or remove dust from the hopper 12. Other secondary support components may also be included as desired or required for effective operation of the hopper 12 and/or other processes.

In certain alternative embodiments, the DEF production system does not include a loading station or opening device for releasing the urea into the hopper or the mixing tank. Rather, in certain embodiments, a urea may be fed directly into the hopper or mixing tank by the user. In certain such embodiments, the urea may be weighed as it is fed to the hopper or the mixing tank. In certain other embodiments, the mixing tank may comprise a sensor for measuring the concentration of the urea, and urea may be fed to the mixing tank until the desired or required concentration of urea is reached.

Water Treatment

Figure 6:
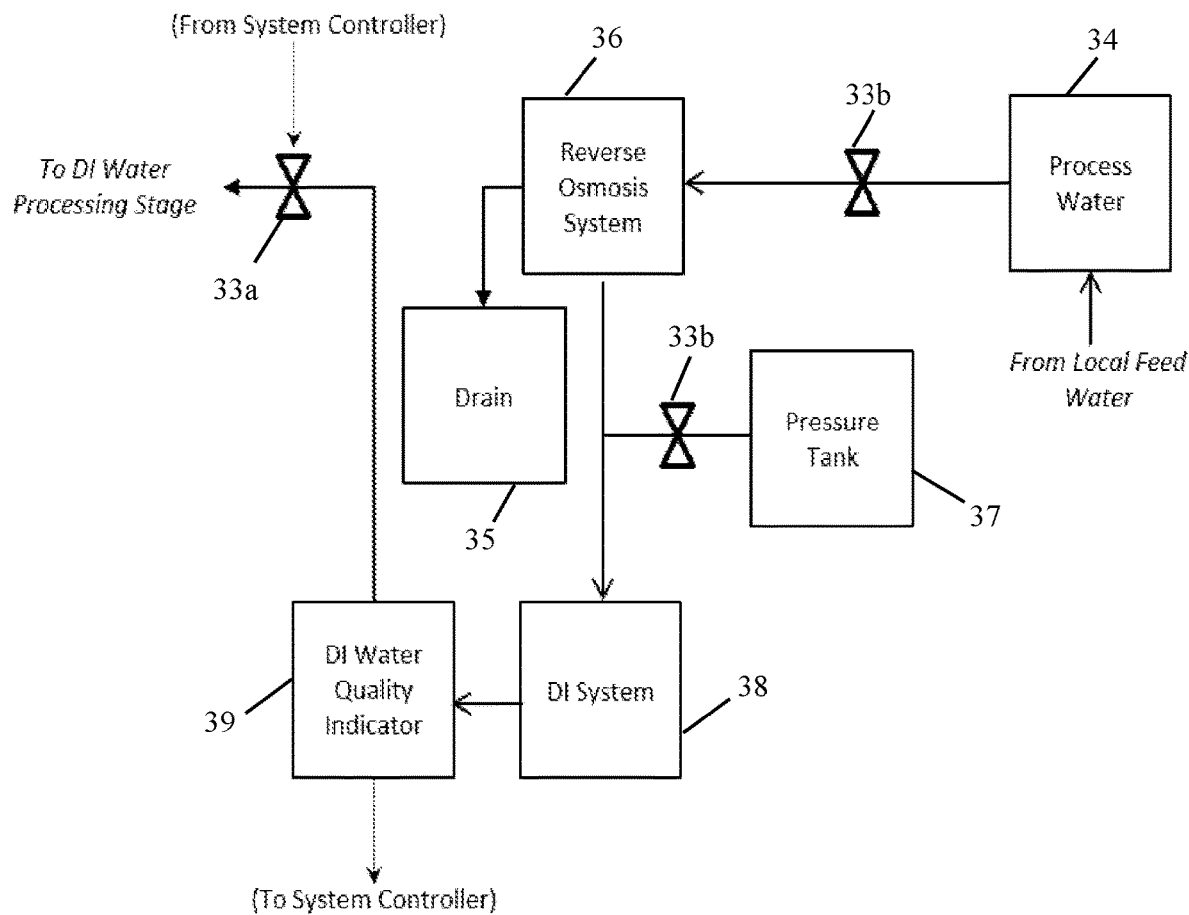
FIG. 6 is a block flow diagram illustrating the main steps of a water treatment process according to one or more embodiments of the present invention.

The water fed to the mixing tank should generally have acceptably low ion, organic, pyrogen, particulate, colloids, and bacteria levels, for example, to produce a DEF product meeting the requirements specified by ISO 22241. Thus, as shown in FIG. 6, in certain embodiments, one or more water treatment processes may be used to provide water having sufficient purity for DEF production. This advantageously allows the water to be locally sourced on-site, for example from a local water supply (e.g., tap water). For example, in certain embodiments, local feedwater is collected 34 from the domiciled location via direct connection to building infrastructure. The water may then be processed through a reverse osmosis ("RO") system 36. The RO process can remove the majority of the feedwater contaminants, leaving only the smallest particles for the downstream deionization ("DI") filter. This process can provide higher purity water and dramatically extend the life of the DI resin. Various RO systems can be used in accordance with embodiments of the present invention. In one preferred embodiment, the RO system 36 utilizes a 4-stage filtering process comprising (consisting of or consisting essentially of) a pre-filter (e.g., about 5-micron), a carbon block filter, a chloramine carbon filter, and an RO membrane. A drain 35 may be utilized to collect the impurities from the RO system. The impurities may be collected in a sediment tank or routed to the local building wastewater infrastructure. In certain embodiments, a pressure tank 37, which may include an internal bladder, is utilized to force flow of the water through the filtering system and avoid additional water pump requirements.

In certain embodiments, the water may be further treated in a deionization ("DI") system 38. The DI system may comprise (consist of or consist essentially of) a dual stage cartridge of DI resin, which can be utilized to deionize the process water prior to mixing. In certain embodiments, a resistivity-based DI water quality meter 39 can be utilized to monitor proper water quality prior to mixing.

The water treatment process may comprise one or more manual and/or automated valves to control water flow through the system. For example, in certain embodiments, an automated valve 33a can control water flow to the mixing chamber. In certain embodiments, various manual valves 33b may also be utilized to isolate systems as needed.

Figure 7:
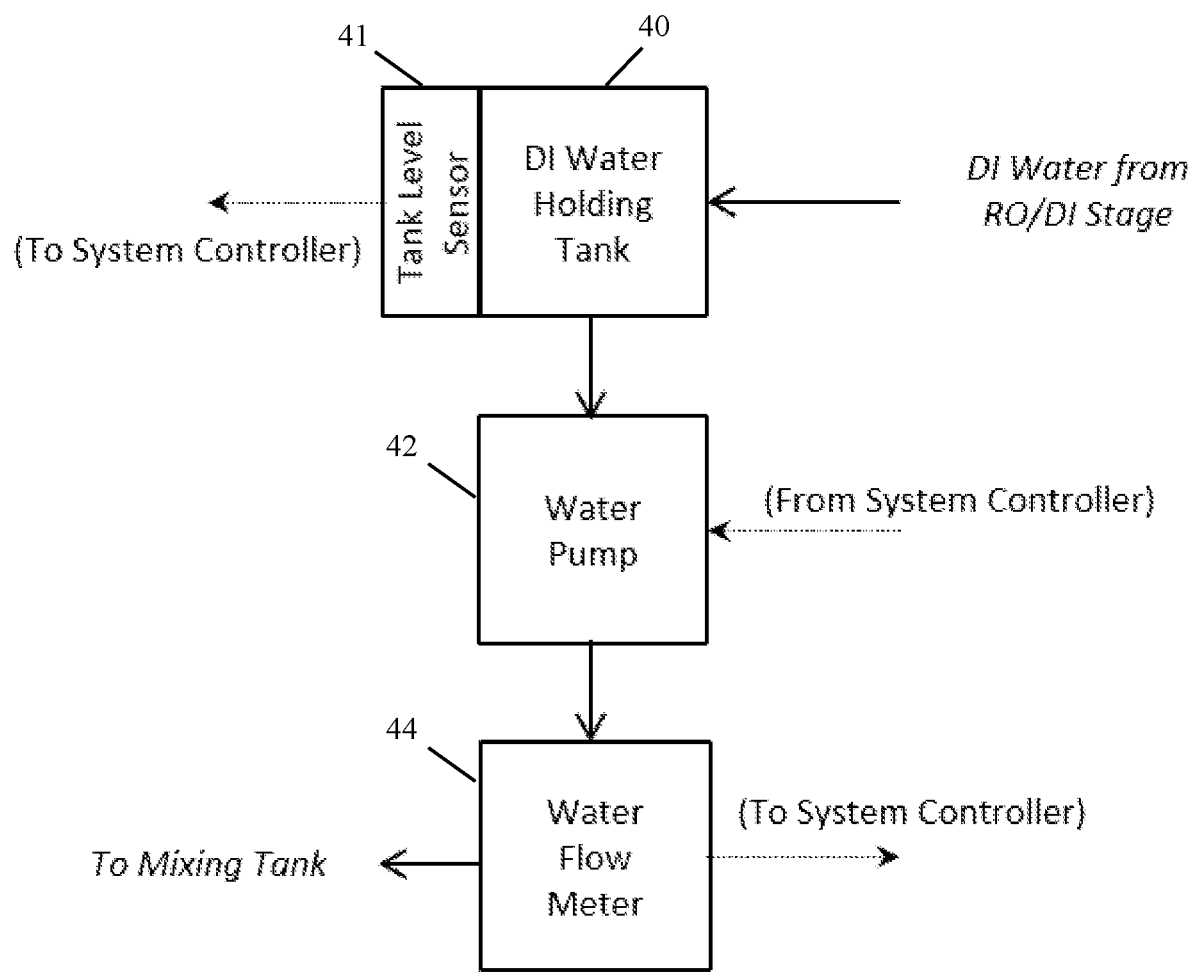
FIG. 7 is a block flow diagram illustrating the main steps of a water flow control process according to one or more embodiments of the present invention.

As shown in FIG. 7, the flow of treated water (i.e., after RO and/or DI processes) may be controlled so as to introduce the desired amount of water into the mixing tank for DEF production. For example, in certain embodiments, a holding tank 40 is located downstream of the water treatment for storing treated water until required. The holding tank 40 may comprise a level sensor 41 to ensure a sufficient amount of treated water is available for DEF production on demand. A water pump 42 and water meter 44 can be located downstream of the holding tank 40 to ensure an appropriate amount of water is delivered to the mixing tank 20 to provide an appropriate ratio of urea-to-water. Alternatively, a calibrated level sensor (not shown) can be used to determine water flow quantities from the water holding tank 40 to the mixing tank 20.

Mixing Tank/DEF Production

Figure 8:
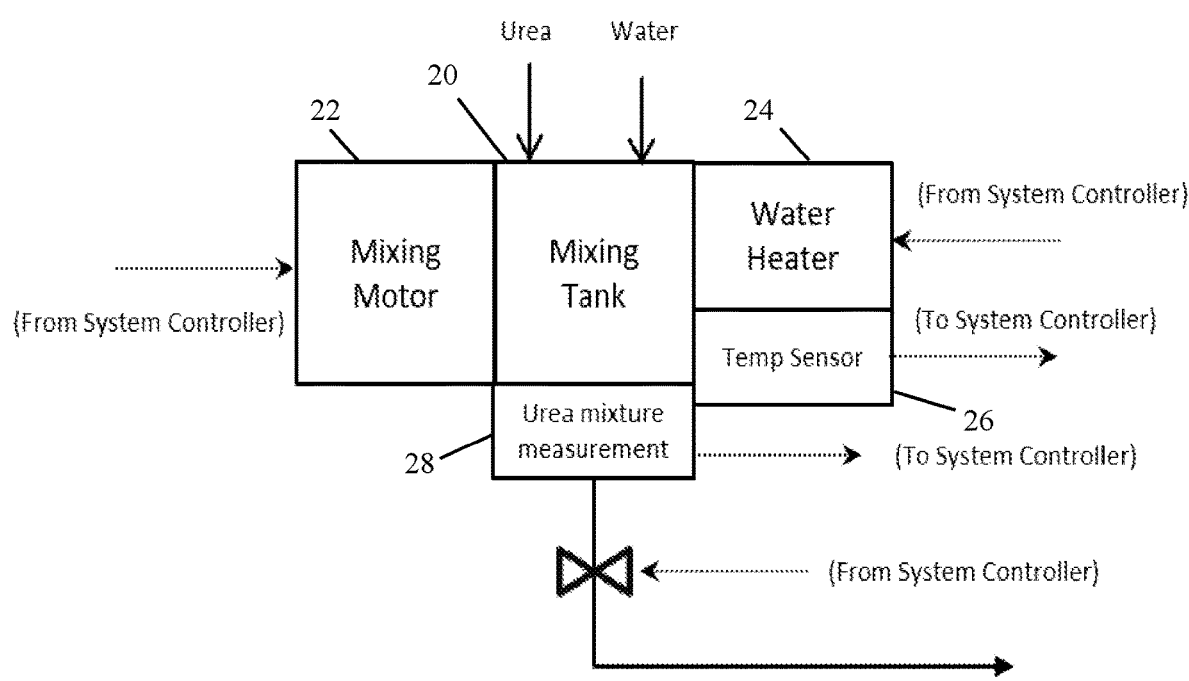
FIG. 8 is a block flow diagram illustrating the main steps of a urea and water mixing system and process to produce DEF according to one or more embodiments of the present invention.

As shown in FIG. 8, in certain embodiments, the mixing tank system comprises (consists of or consists essentially of) a mixing tank 20, a mixing motor 22, a water heater 24, a temperature sensor 26, and a urea concentration measurement device 28 (e.g., a refractometer). The mixing tank may comprise any of a variety of materials, geometries, and sizes, depending on the volume of the DEF batch being produced. In certain embodiments, the mixing tank comprises a motor-driven mixing paddle or similar mixer device. In certain embodiments, the mixing tank comprises one or more vertical baffles to inhibit vortex(es) from forming in the solution during mixing.

The urea and water (which may be sourced from one or more of the upstream processed described above) are introduced into the mixing tank 20 and mixed until solubility (i.e., until the urea is dissolved) and/or desired urea concentration is achieved, thereby producing the DEF product. In certain embodiments, the urea and the water are fed into the mixing tank at a ratio of about 1:2 urea-to-water, although other urea-to-water ratios may be fed into the mixing tank depending on the desired urea concentration or specification of the DEF product. Upon dissolution of the urea in water, an endothermic reaction occurs, which acts to cool the solution. Thus, the water heater 24 may be used to heat the solution to improve solubility and reduce processing time. A variety of water heaters may be used, such as jacket and/or internal coil systems. In certain embodiments, the urea and water are mixed at an average temperature of about 150° F. to about 200° F., preferably about 170° F. to about 175° F.

As noted above, the urea may be provided in a pre-measured quantity. This pre-measured quantity ensures an appropriate weight ratio of urea-to-water so as to achieve the desired or required urea concentration in the DEF product. In certain embodiments, the pre-measured quantity can be selected to meet the DEF product specifications, for example, as specified by ISO 22241. In particular, in certain embodiments, the pre-measured quantity of urea and water may be mixed at an appropriate ratio so as to provide a DEF product comprising 32.5% to 33.2% by weight of urea. In certain embodiments, the DEF has a density at 77° F. of about 9.05 to 9.09 lbs/gallons, a refractive index at 77° F. of about 1.2814 to 1.3843, and/or impurity levels below those specified by ISO 22241.

Figure 9:
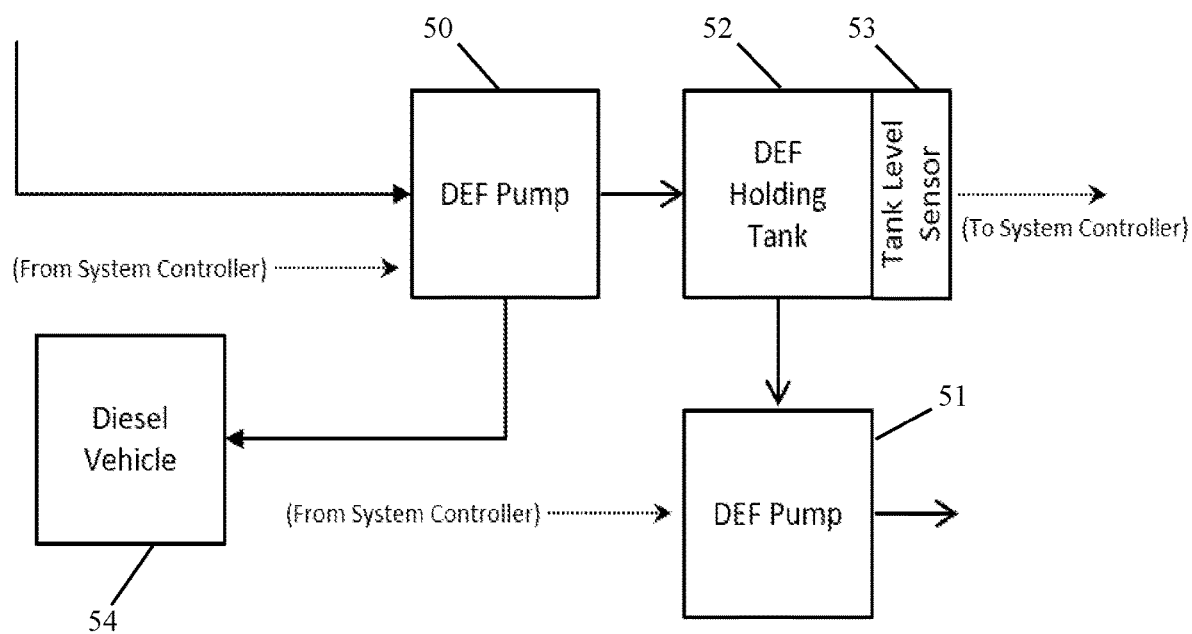
FIG. 9 is a block flow diagram illustrating the main steps of DEF distribution system and process according to one or more embodiments of the present invention.

As shown in FIG. 9, upon completion of mixing and DEF production, at least a portion of the DEF product can be pumped 50 to a DEF holding tank 52 for intermediate storage. In certain embodiments, the DEF holding tank 52 is located proximate to the mixing tank 20. For example, in certain embodiments, the DEF holding tank 52 may be located within 1 mile, within 1,000 feet, within 100 feet, within 50 feet, or within 10 feet of the mixing tank 20. In certain embodiments, the DEF holding tank 52 comprises a level sensor 53 to lockout overflow issues and trigger new batch production as needed. The DEF product can be removed from the tank using a pump 51 and/or other ordinary electric or manual methods known in the art.

Additionally, or alternatively, at least a portion of the DEF product may be dispensed directly into a diesel vehicle 54 without being introduced or stored in an intermediate storage vessel. For example, the pump 50 may direct the DEF product through a conduit inserted by a user to dispense the DEF product into a tank of the diesel vehicle 54. This advantageously provides for fresh, on-demand DEF for immediate use. Thus, in certain embodiments, the processes and systems described herein may advantageously be operated by a single user, including loading of a container comprising a pre-measured quantity of urea into the system and dispensing of the DEF product directly into a diesel vehicle.

In certain embodiments, the DEF may be used with, or dispensed directly into, any diesel-powered vehicle utilizing DEF, including, but not limited to, engine motor vehicles (cars, trucks, buses, motorcycles, tractors, etc.), railed vehicles (trains, trams, etc.), watercraft (ships, boats, etc.), amphibious vehicles (screw-propelled vehicles, hovercraft, etc.), aircraft (airplanes, helicopters, etc.), and the like.

Power Requirements and System Controller

Figure 10:
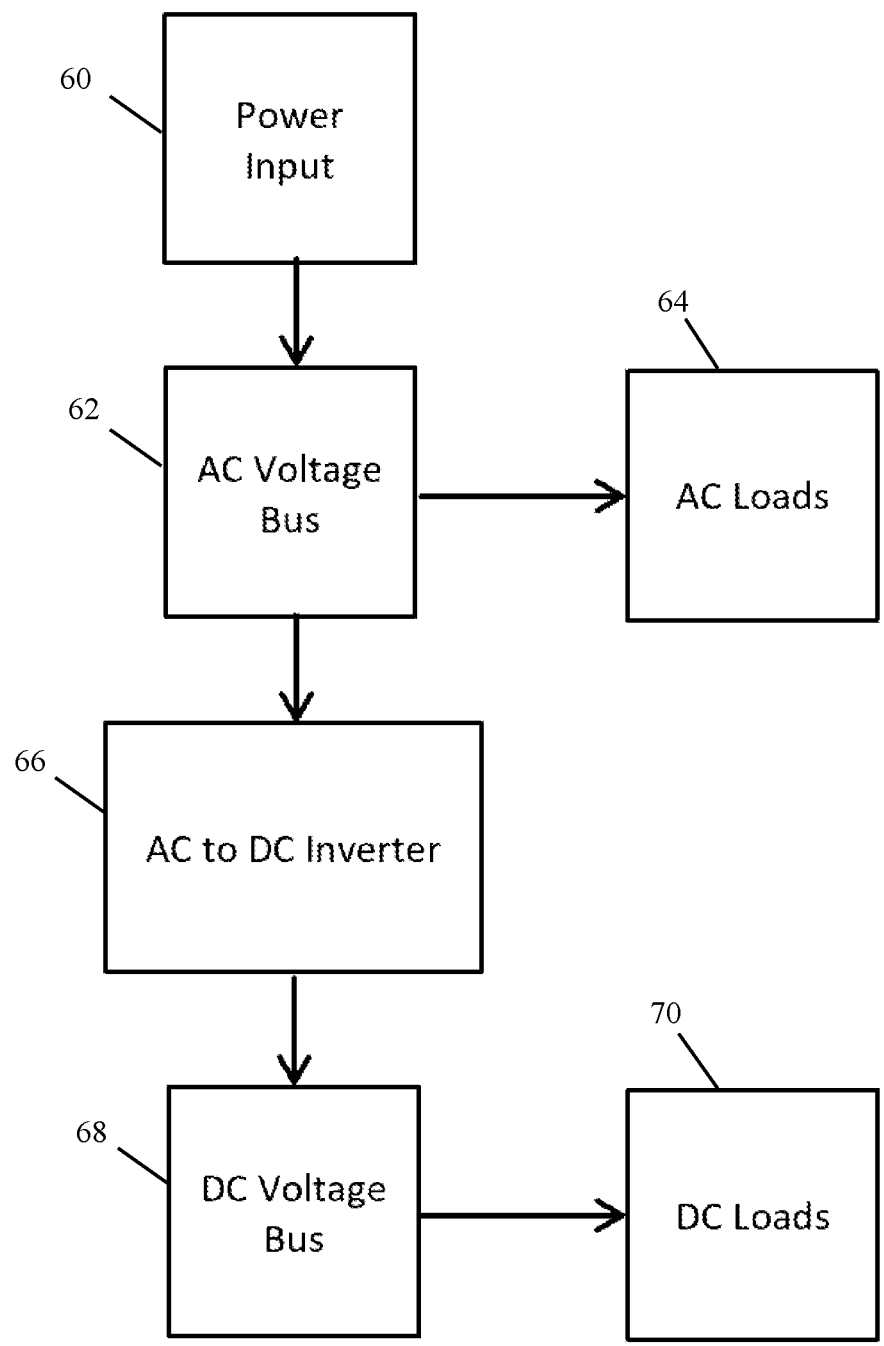
FIG. 10 is a block flow diagram illustrating the main steps of a power input, conversion, and distribution system and process according to one or more embodiments of the present invention.

Embodiments of the present invention can effectively be implemented at a variety of power handling levels, which can depend on the particular application and location. As shown in FIG. 10, in certain embodiments, the processes and systems described herein may be configured to utilize a power input 60, which can be AC power, for example, from a power grid. In certain embodiments, power input 60 comprises 110 VAC to 480 VAC, or 120 VAC to 260 VAC. A AC voltage bus 62 may be used to direct the power input 60 to components requiring 110 VAC to 480 VAC, or 120 VAC to 260 VAC loads 64. An inverter 66 may be used to convert alternating current voltage to direct current voltage, which in certain embodiments may be 12 VDC to 48 VDC. A DC voltage bus 68 may be used to direct DC power to components requiring 12 VDC to 48 VDC loads 70. For example, 12 VDC to 48 VDC may be used to protect equipment and processes in the event of power loss, as well as to absorb current surges from process equipment.

Figure 11:
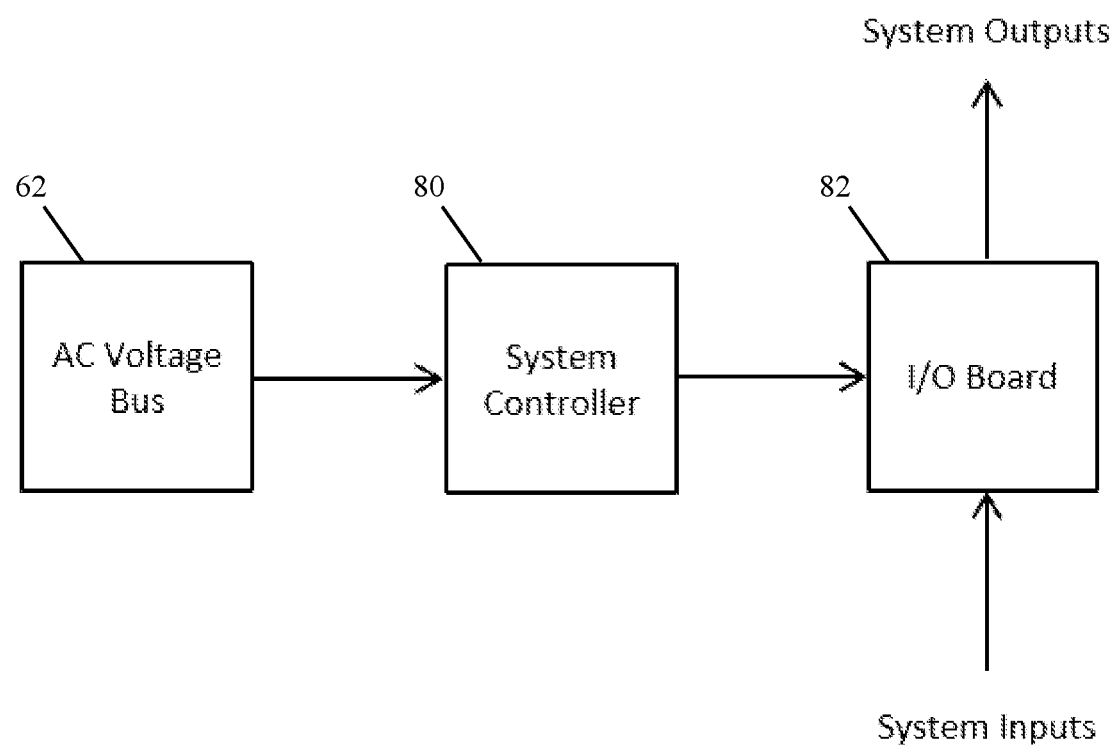
FIG. 11 is a block flow diagram illustrating the main steps of a system controller system and process according to one or more embodiments of the present invention.

As shown in FIG. 11, in certain embodiments, a system controller 80 comprising (consisting of or consisting essentially of) an I/O board 82 may be used to microprocess, regulate, and/or control one or more processes or systems described above. In certain embodiments, the system controller 80 may receive power from the AC voltage bus 62.

Uses and Advantages

Embodiments of the present invention have notable advantages over existing technologies. For example, current state-of-the-art DEF production processes only includes mixing and producing larger volume batches of DEF, for example, greater than hundreds of gallons, which is then packaged and shipped. The processes and systems in accordance with embodiments of the present invention advantageously mix and produce DEF in smaller quantities to enable production at the point of use. For example, in certain embodiments, the processes and systems described herein may be used to produce a DEF product in batches of about 1 gallon to about 100 gallons, preferably about 2 gallons to about 55 gallons, which may be stored in a nearby intermediate holding tank and/or dispensed directly into a diesel vehicle. This application can allow the use of smaller sized equipment and overall footprint of the system. For example, in certain embodiments, the conduits (e.g., pipes, hoses, etc.) fluidly connecting one or more of the systems, apparatuses, or processes described herein may have a diameter of about ¼ inch to about 1 inch. Additionally, in certain embodiments, the various holding tanks and other fluid vessels may have a capacity volume of about 1 gallon to about 100 gallons, or about 2 gallons to about 55 gallons. This application also reduces the shipment costs associated with water and provides fresh diesel-exhaust-fluid with the longest potential shelf life or for immediate use. Additionally, this production model allows the end user to completely eliminate storage concerns, as DEF is only produced on a short-term, as-needed basis. The systems and processes according to embodiments of the present invention may therefore be particularly suitable for medium-sized, diesel fleet operators, for example, with approximately 10 to 250 diesel vehicles in a single location.

Additional advantages of the various embodiments of the invention will be apparent to those skilled in the art upon review of the disclosure herein and the working examples below. It will be appreciated that the various embodiments described herein are not necessarily mutually exclusive unless otherwise indicated herein. For example, a feature described or depicted in one embodiment may also be included in other embodiments, but is not necessarily included. Thus, the present invention encompasses a variety of combinations and/or integrations of the specific embodiments described herein.

As used herein, the phrase "and/or," when used in a list of two or more items, means that any one of the listed items can be employed by itself or any combination of two or more of the listed items can be employed. For example, if a composition is described as containing or excluding components A, B, and/or C, the composition can contain or exclude A alone; B alone; C alone; A and B in combination; A and C in combination; B and C in combination; or A, B, and C in combination.

The present description also uses numerical ranges to quantify certain parameters relating to various embodiments of the invention. It should be understood that when numerical ranges are provided, such ranges are to be construed as providing literal support for claim limitations that only recite the lower value of the range as well as claim limitations that only recite the upper value of the range. For example, a disclosed numerical range of about 10 to about 100 provides literal support for a claim reciting "greater than about 10" (with no upper bounds) and a claim reciting "less than about 100" (with no lower bounds).

Further, the description of the embodiments disclosed herein may refer to various relative orientations, such as top, bottom, side, and the like. These terms are used for convenience of description and are not intended to limit the scope of the invention in any way. Unless stated otherwise, these relative terms do not require the equipment to be constructed or operated in a particular orientation.

Additionally, various systems, apparatuses, and processes are described herein and shown in the drawings. It should be understood that these systems, apparatuses, and processes may comprise individual, separate systems, apparatuses, and processes, or may comprise one or more of these systems, apparatuses, and processes combined into a single system, apparatus, or process. The various systems, apparatuses, and processes may be directly or indirectly connected or coupled (including fluidly connected or coupled) using any of a variety of conduits and attachment or coupling mechanisms.

The invention claimed is:

1. A process for producing diesel exhaust fluid, the process comprising:
   securing a container comprising a pre-measured quantity of urea into a loading station;
   directing, via a system controller, an opening device to form openings in top and bottom surfaces of the container;
   directing, via the system controller, a water pump to feed water through the container;
   feeding the urea and water into a mixing tank;

directing, via the system controller, a motor to activate to mix the urea and the water in the mixing tank to produce a volume of 1 gallon to 100 gallons of the diesel exhaust fluid; and directing, via the system controller, one or more diesel exhaust fluid pumps to flow the diesel exhaust fluid in two or more different directions including a first direction in which the diesel exhaust fluid flows directly into a diesel vehicle for use and a second direction in which the diesel exhaust fluid flows into a diesel exhaust fluid holding tank.

2. The process of claim 1, wherein the feeding the urea into the mixing tank comprises collecting the urea released from the container in a hopper and dispensing the urea from the hopper into the mixing tank.

3. The process of claim 1, wherein the forming the openings comprises piercing, ripping, cutting, and/or tearing the container.

4. The process of claim 3, wherein the forming the openings comprises inserting a rod into the container, thereby piercing the container.

5. The process of claim 1, wherein the pre-measured quantity of urea is in the form of powder, prills, pellets, and/or granules.

6. The process of claim 1, wherein the container consists essentially of the pre-measured quantity of urea.

7. The process of claim 1, wherein the pre-measured quantity of urea has a purity of at least 99% by weight.

8. The process of claim 1, wherein the urea and the water are fed into the mixing tank at a weight ratio of about 1:2 urea-to-water.

9. The process of claim 1, wherein the water is treated in a reverse osmosis and/or deionization system before feeding into the mixing tank.

10. A diesel exhaust fluid production system comprising:
a loading station configured to receive and secure a container comprising a pre-measured quantity of urea;
an opening device configured to form an opening in the container, thereby releasing the pre-measured quantity of urea;
a mixing tank configured to receive and mix the urea and water to produce a volume of 1 gallon to 100 gallons of diesel exhaust fluid product;
a water pump configured to flow water through the container;
one or more diesel exhaust fluid pumps configured to flow the diesel exhaust fluid in two or more different directions including a first direction in which the diesel exhaust fluid flows directly into a diesel vehicle for use and a second direction in which the diesel exhaust fluid flows into diesel exhaust fluid holding tank; and
a system controller configured to: direct the opening device to form openings in top and bottom surfaces of the container,
direct the water pump to feed water through the container,
direct a motor of the mixing tank to mix the urea and the water in the mixing tank, and
direct the one or more diesel exhaust fluid pumps to flow the diesel exhaust fluid into the diesel vehicle for use and the diesel exhaust fluid holding tank.

11. The system of claim 10, wherein the opening device comprises a rod configured to pierce the container.

12. The system of claim 10, further comprising a hopper configured to collect the urea released from the container and feed the urea to the mixing tank.

* * * * *